(12) United States Patent
Nardi (10) Patent No.: US 7,367,959 B2
(45) Date of Patent: May 6, 2008

(54) DEVICE FOR CARDIOCIRCULATORY ASSISTANCE

(75) Inventor: Giancarlo Nardi, Pisa (IT)

(73) Assignee: A.N.B. Technology S.R.L., Leghorn (IT)

( * ) Notice: Subject to any disclaimer, the term of this patent is extended or adjusted under 35 U.S.C. 154(b) by 0 days.

(21) Appl. No.: 11/484,595

(22) Filed: Jul. 12, 2006

(65) Prior Publication Data
US 2007/0021646 A1    Jan. 25, 2007

(30) Foreign Application Priority Data
Jul. 22, 2005    (IT)    .......................... MI2005A1420

(51) Int. Cl.
*A61M 35/00*    (2006.01)
(52) U.S. Cl. .................. 604/4.01; 604/33; 604/28; 604/509; 600/17; 600/18; 417/356
(58) Field of Classification Search .............. 604/4.01, 604/33, 28, 509; 600/17, 18; 417/356
See application file for complete search history.

(56) References Cited

U.S. PATENT DOCUMENTS 4,183,357 A * 1/1980 Bentley et al. ............. 604/175
4,782,817 A * 11/1988 Singh et al. ................. 600/17
5,676,651 A * 10/1997 Larson et al. ................ 604/33
6,752,602 B2 * 6/2004 Schulte Eistrup et al. .. 417/356
7,125,376 B2 * 10/2006 Viole et al. .................. 600/16

OTHER PUBLICATIONS

Medtronic, Inc. (Bio-Pump® Plus Centrifugal Blood Pump Information), Jan. 1998.*
CATS—Computation of Blood Flow in the Baylor Gyro Pump, 2000.*

* cited by examiner

*Primary Examiner*—Tatyana Zalukaeva
*Assistant Examiner*—Ilya Y Treyger
(74) *Attorney, Agent, or Firm*—Wenderoth, Lind & Ponack, L.L.P.

(57) ABSTRACT

A device for cardiocirculatory assistance, also named a ventricular assist device, includes a haematic pump (50) with a pump body (7) having an inner space (21) defined by a rigid structure (51) and a pair of mobile membranes (16, 17) alternately driven in opposite directions by alternately positive pressure and negative pressure gas supplied to recesses (19, 20) surrounding the two membranes by means of an external pneumatic force generating unit (1). This device achieves excellent operation results while maintaining a reduced size and reduced weight.

20 Claims, 7 Drawing Sheets

DEVICE FOR CARDIOCIRCULATORY ASSISTANCE

FIELD OF THE INVENTION

The present invention relates to a device for cardiocirculatory assistance which is obtained by means of a special haematic pump driven by pneumatic energy.

BACKGROUND OF THE INVENTION

It is known that in heart-surgery practice some devices for the mechanical assistance of the heart are used, commonly indicated as "ventricular assist devices (V.A.D.)" or "total artificial hearts (T.A.H.)".

These are essentially devices adapted to mechanically pump blood to produce pulsing or continuous blood flows.

Such devices are employed to solve acute reversible heart failure clinical cases (as infarct or myocarditis) or are used to support the circulatory function while waiting for a heart transplant.

There have been for years several both left and right ventricular assist devices or biventricular assist devices (T.A.H); some of them are commercially available, others have been developed only at an experimental stage.

In most cases, the currently existing devices exhibit some difficulties to be accommodated inside the chest, because of problems both with size and weight.

Other drawbacks that can be found therein are caused by their inner configurations and their pumping modes, which may induce haemolysis or blood clot formation.

Some solutions currently use a balloon (ventricular sac) or a single membrane as a blood contacting flexible element. These devices, as their inherent feature, do not allow blood circulation in the pump, thus avoiding the above mentioned problems. Another negative aspect of these currently available solutions is represented by the weight and size of the driving units associated with the pumping device, which render the portability, namely the easy transport by the patient, essentially non-existent.

SUMMARY OF THE INVENTION

In view of this state of the art, it was the object of the present invention to obtain a device for cardiocirculatory assistance exhibiting high reliability and having reduced weight and size.

In accordance with the present invention, such an object is achieved by a device for cardiocirculatory assistance characterised in that it comprises a haematic pump with a pump body having an inner space defined by a rigid structure and a pair of opposed position mobile membranes, a pair of rigid lids defining around the mobile membranes respective recesses supplied with alternately positive pressure and negative pressure gas by an external pulsing pneumatic energy generating unit, so as to alternately draw the mobile membranes reciprocally together and apart in order to respectively decrease and increase the volume of the inner space of the pump body. The devise also comprises a blood input tubing in the inner space of the pump body, a blood output tubing from the inner space and a pair of spontaneously opening one-way valves respectively associated to the tubings in order to allow, in combination with the volume variation of the inner space of the pump body induced by the alternate motion of the two membranes, a continuous filling and evacuating cycle of the inner space of the pump body, therefore generating a blood flow rate depending on the number of pulses provided by the external pneumatic energy generating unit.

By means of its special two-membrane pumping system, the haematic pump comprised in the device according to the invention, allows to obtain a particularly efficient and effective haematic flow, as well as exhibiting high reliability, also obtaining on the whole a device having no inertial sussultatory motions, where the periodically pulsing haematic flow provides pulses, which may be synchronous or asynchronous with respect to the heart pulse, the whole driven by an external pneumatic energy generating unit which may have reduced weight and reduced size.

BRIEF DESCRIPTION OF THE DRAWINGS

A specific embodiment of the invention will now be described in detail, by way of a non-limiting example, with reference to the attached figures, in which.

DETAILED DESCRIPTION OF PREFERRED EMBODIMENTS

Figure 1:
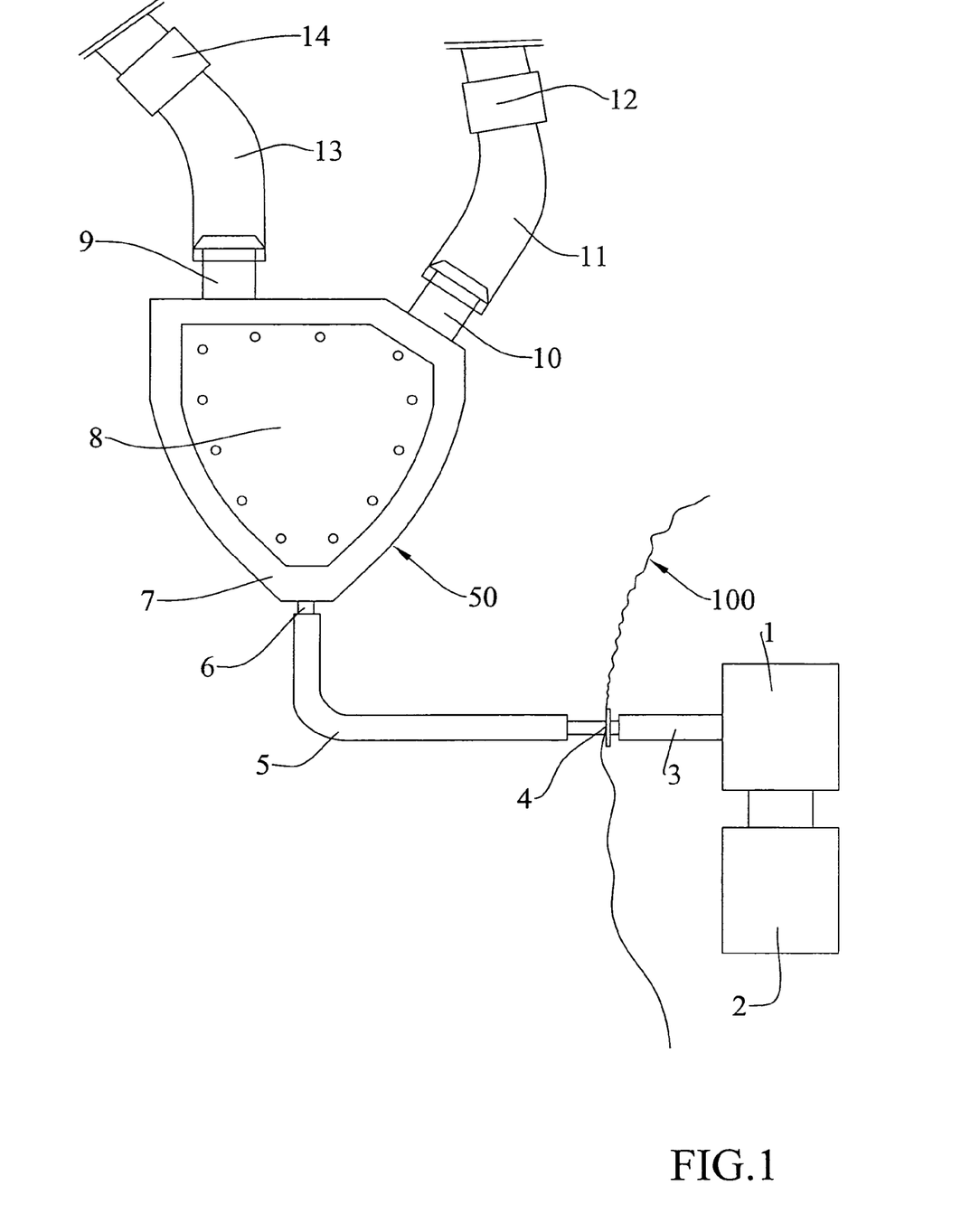
FIG. 1 shows a diagrammatic view of a device for cardiocirculatory assistance according to the invention.

FIG. 1 shows a diagrammatic drawing of the various components of a device for cardiocirculatory assistance according to the present invention.

The device comprises a pneumatic energy (gas) generating unit 1 supplied by a battery set 2, which transmits pneumatic energy to a tube 5 positioned inside the body of the patient (generally indicated by reference number 100) through a flexible tube 3 and a transcutaneous implant 4.

Figure 2:
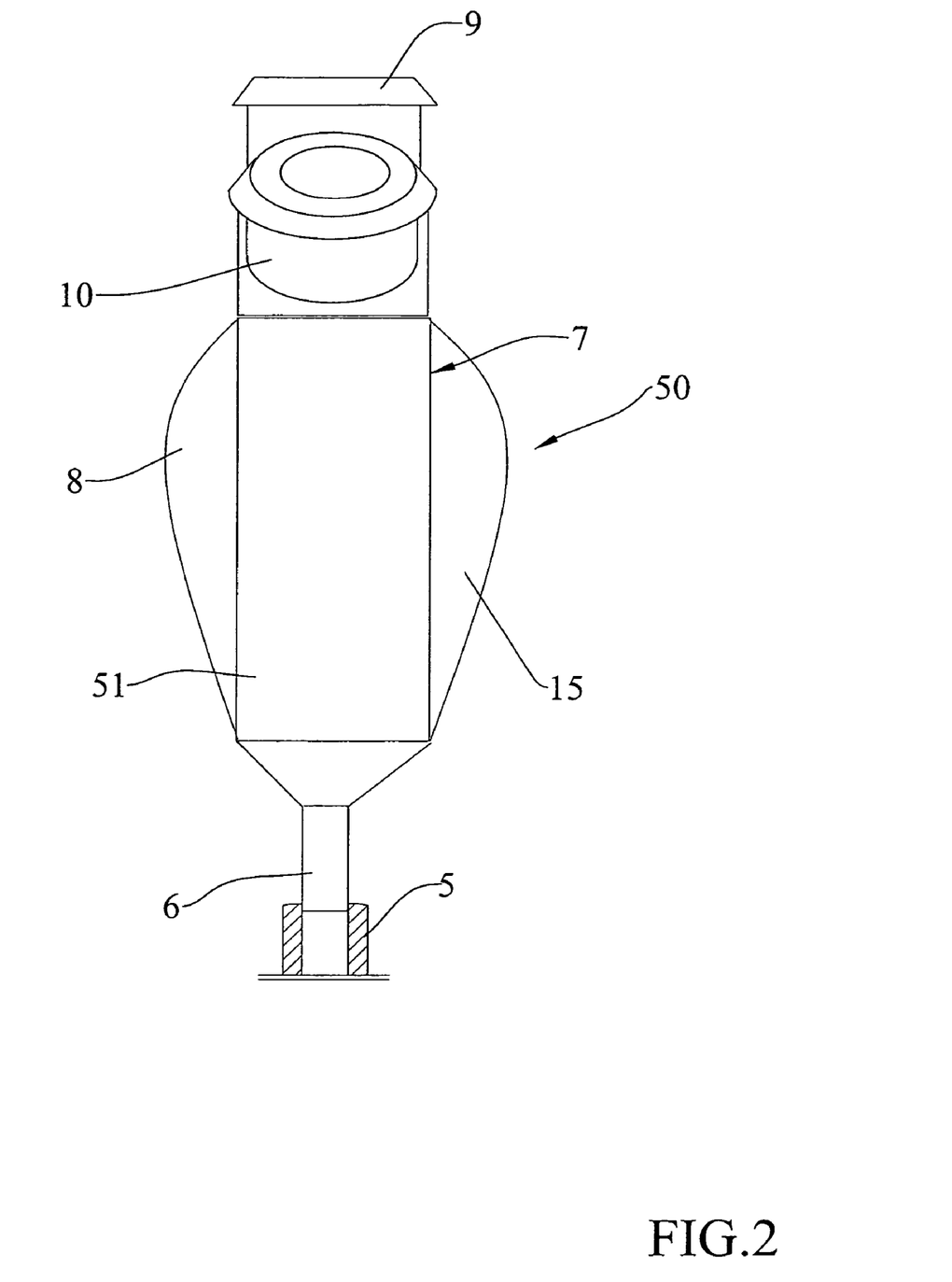
FIG. 2 shows a side view of the haematic pump comprised in the device of FIG. 1, with the membranes shown in a resting position.
Figure 3:
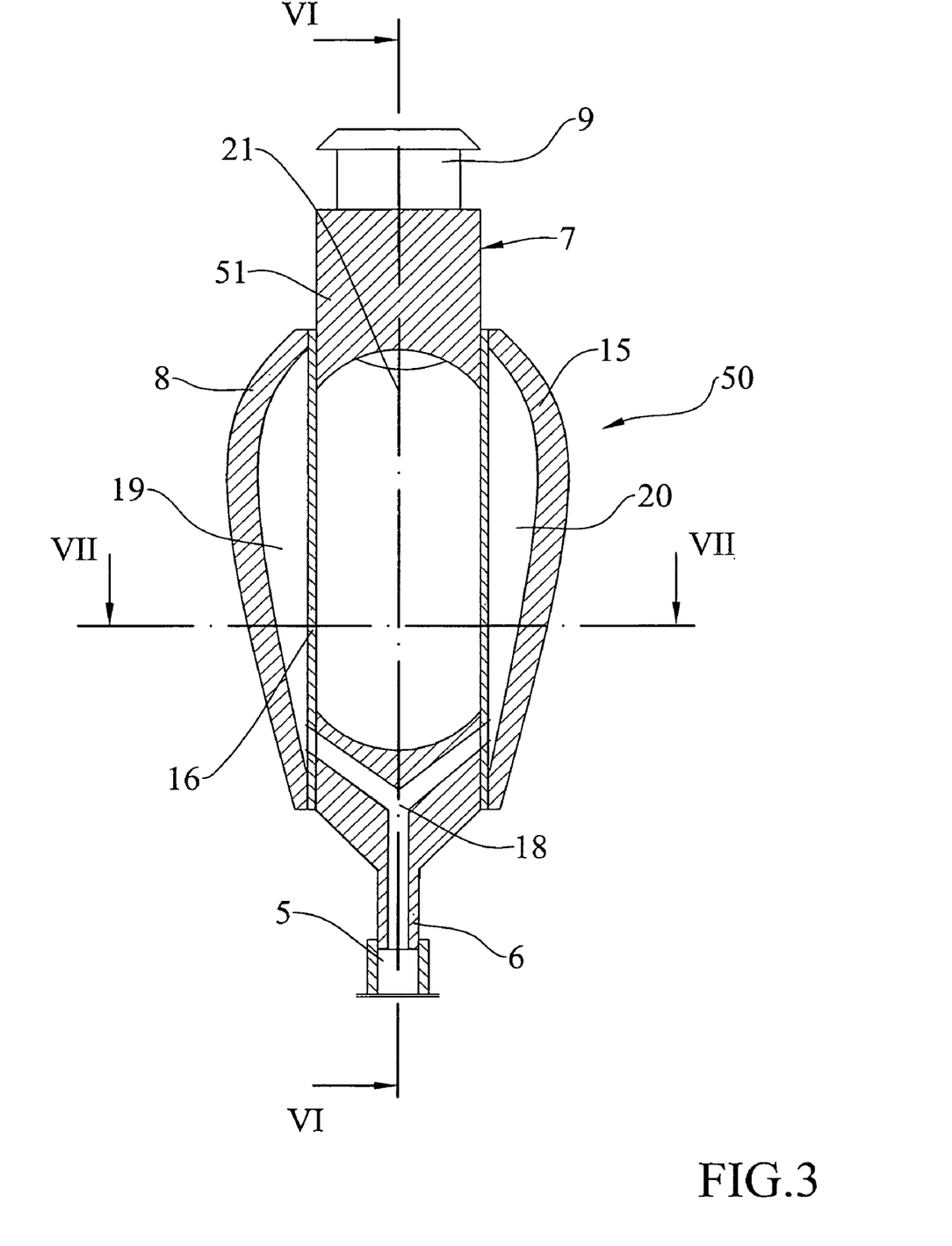
FIG. 3 shows a longitudinal section of the haematic pump in a plane parallel to that of FIG. 2, with the pump shown in the resting position.

The inner tube 5 is connected to an input 6 of a haematic pump 50 having a pump body 7 in a haemocompatible material sealed between two rigid protective lids 8 and 15, obtainable in a material compatible with the body tissues of the patient, reciprocally fixed so as to form a single piece, as shown in FIGS. 1, 2 and 3.

Between the two lids 8 and 15, the pump body 7 envisages two flexible inner membranes 16 and 17 (FIG. 3), defining a substantially cylindrical shaped inner space 21 together with a remaining rigid structure 51 (FIGS. 3, 6 and 7), communicating with an inlet 9 and an outlet 10, to which respective haemocompatible tubings 13 and 11 commonly used in heart surgery techniques are connected (FIG. 1), where there are housed two automatic one-way valves 12 and 14, named spontaneously opening valves, commonly used in valve replacement surgery.

Under the control of the automatic valve 14, tubing 13 withdraws blood from an atrium of the heart (e.g. through an atrioventricular tube) or from other areas of the cardiovascular system and inputs it in the inner space 21 of the haematic pump 50, which pushes the blood itself to the blood vessels of the systemic circulation and pulmonary circulation through the other tubing 11 provided with automatic valve 12.

FIG. 3 shows a longitudinal section of the haematic pump 50 in a resting position.

In operation, through connection 6 and an inner channelling 18 of the pump body 7, a gas from generator 1 and from tubes 3 and 5 (named operating gas) is initially inputted inside two recesses 19 and 20 defined between the two flexible membranes 16 and 17 and the two rigid lids 8 and 15 and then in-taken from the recesses.

The blood in inner space 21 of the pump body 7 does not contact the compressed gas generated by the pneumatic energy external unit 1 as it is separated from it by means of two mobile membranes 16 and 17.

In turn, the two lids 8 and 15 avoid contact between the working gas and the body tissues of the patient. Their resistance also allows an efficient protection against knocks and any handling action exerted on pump 50.

Figure 4:
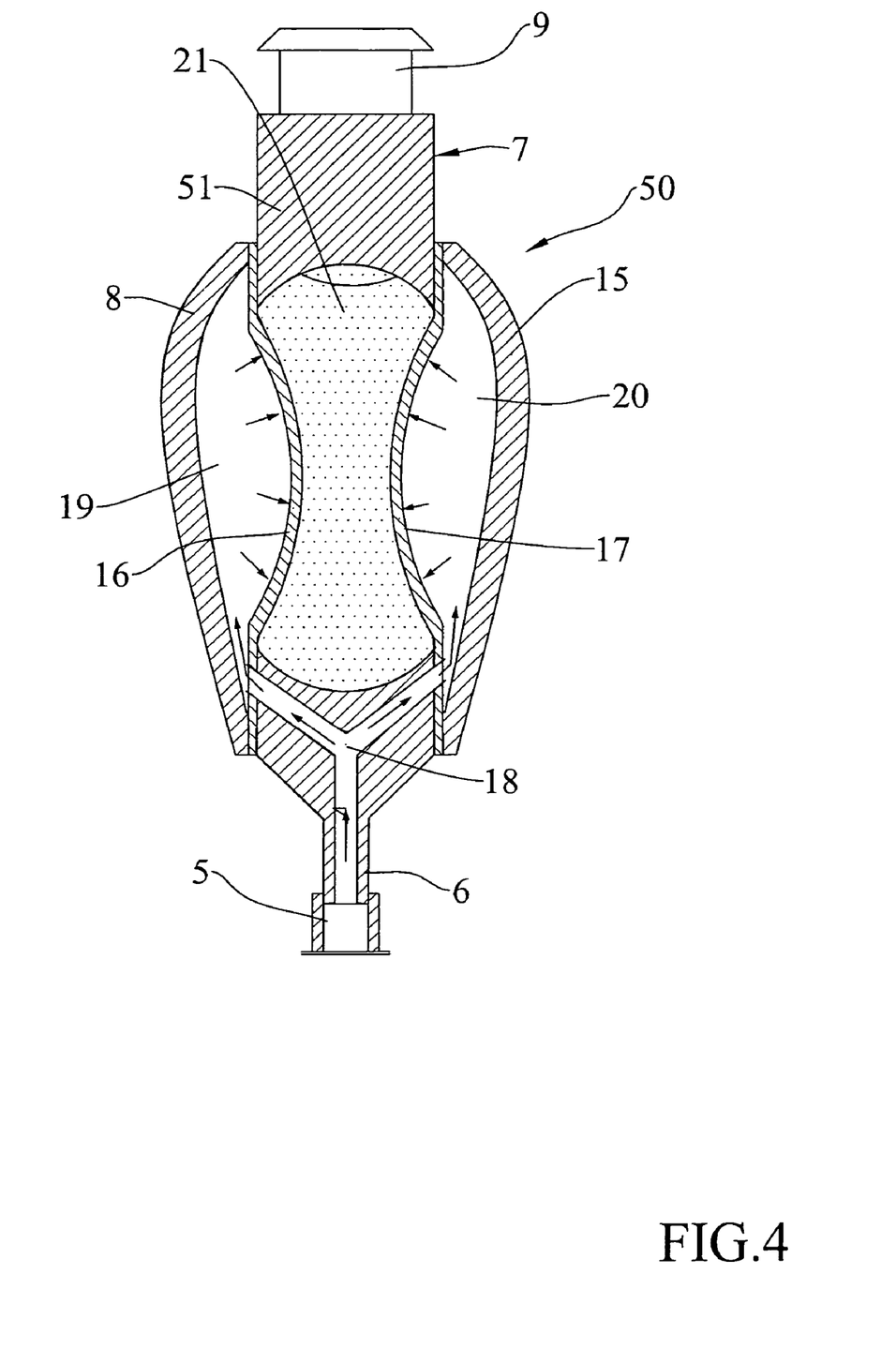
FIG. 4 shows a similar longitudinal section of the haematic pump during a delivery or compression step.

As shown in FIG. 4, haematic pump 50 comprises a compression or delivery step, in which gas deriving from the pneumatic energy external generator 1 of FIG. 1 is pushed inside the two recesses 19 and 20 through channelling 18. The compressed gas inputted in recesses 19 and 20 pushes the mobile membranes 16 and 17 towards each other and towards the inside of the pump thus inducing a decrease of the inner space 21.

The blood contained therein no longer finding a space to occupy, is thus forced to leave the pump body through the only available aperture, the one obtained at outlet 10 (FIG. 6), from which tubing 11 provided with automatic one-way valve 12 (FIG. 1) allows the blood to flow to the systemic or pulmonary circulation.

Figure 5:
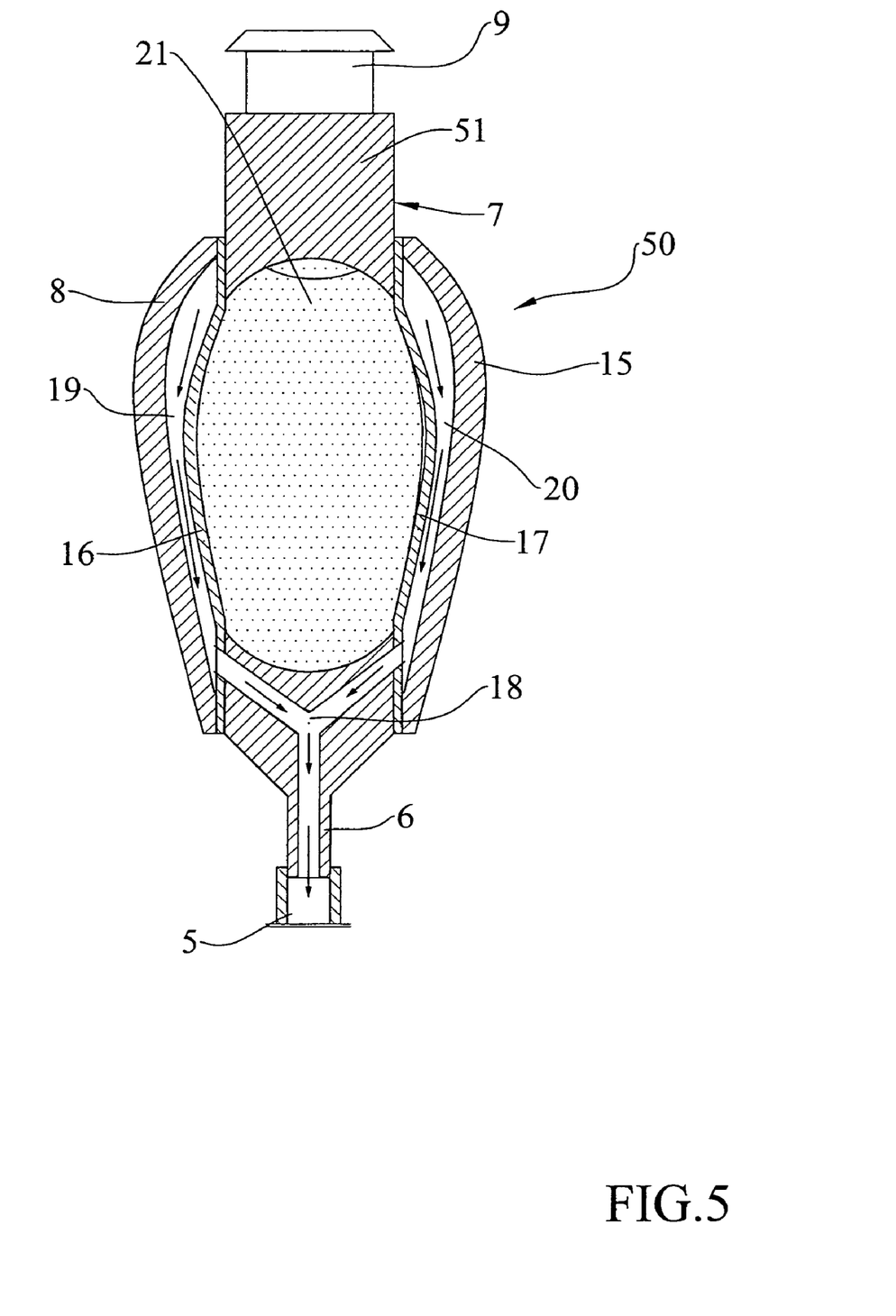
FIG. 5 shows a similar longitudinal section of the haematic pump during a suction or filling step.

FIG. 5 shows a section of the haematic pump in a following suction or filling step. In this step, gas is in-taken from the two chambers 19 and 20 by the external pneumatic energy generator 1 through conduit 18 and tubings 5 and 3 connected thereto by means of connection 6.

The evacuation of the working gas from the two chambers 19 and 20 determines the motion of the two membranes 16 and 17 in a direction opposite to that of the compression or delivery step, namely an outward direction, thus inducing an increase of the inner space 21 of the pump body 7.

This exclusively blood-occupied volume draws from the outside, by increasing its capacity, more blood that enters space 21 through inlet aperture 9 and tubing 13, where valve 14 of FIG. 1 automatically opens to allow a one-way blood flow directed inside the pump body.

As already mentioned, both valves 14 and 12 are one-way flow and spontaneously opening, namely their aperture occurs automatically depending on the blood flow direction in the respective connection tubings 13 and 11, and therefore on the pressure in inner space 21 of the pump. More precisely, valve 14 opens if the pump draws blood into inner space 21 and closes if the blood flow tends to invert its direction, whereas valve 12 operates in an opposite way, by closing when blood moves inside the pump and opening if blood is pushed out of the pump itself.

The above described operation steps with reference to FIGS. 5 and 4 alternately follow each other so as to generate a continuous blood suction and delivery cycle, which allows the haematic pump to operate as a mechanical servo system to the heart.

During such cycle, the two membranes 16 and 17 are subjected to homogenous radial tensions, which render the cycle itself regular and preserve the membranes from premature wear.

Figure 6:
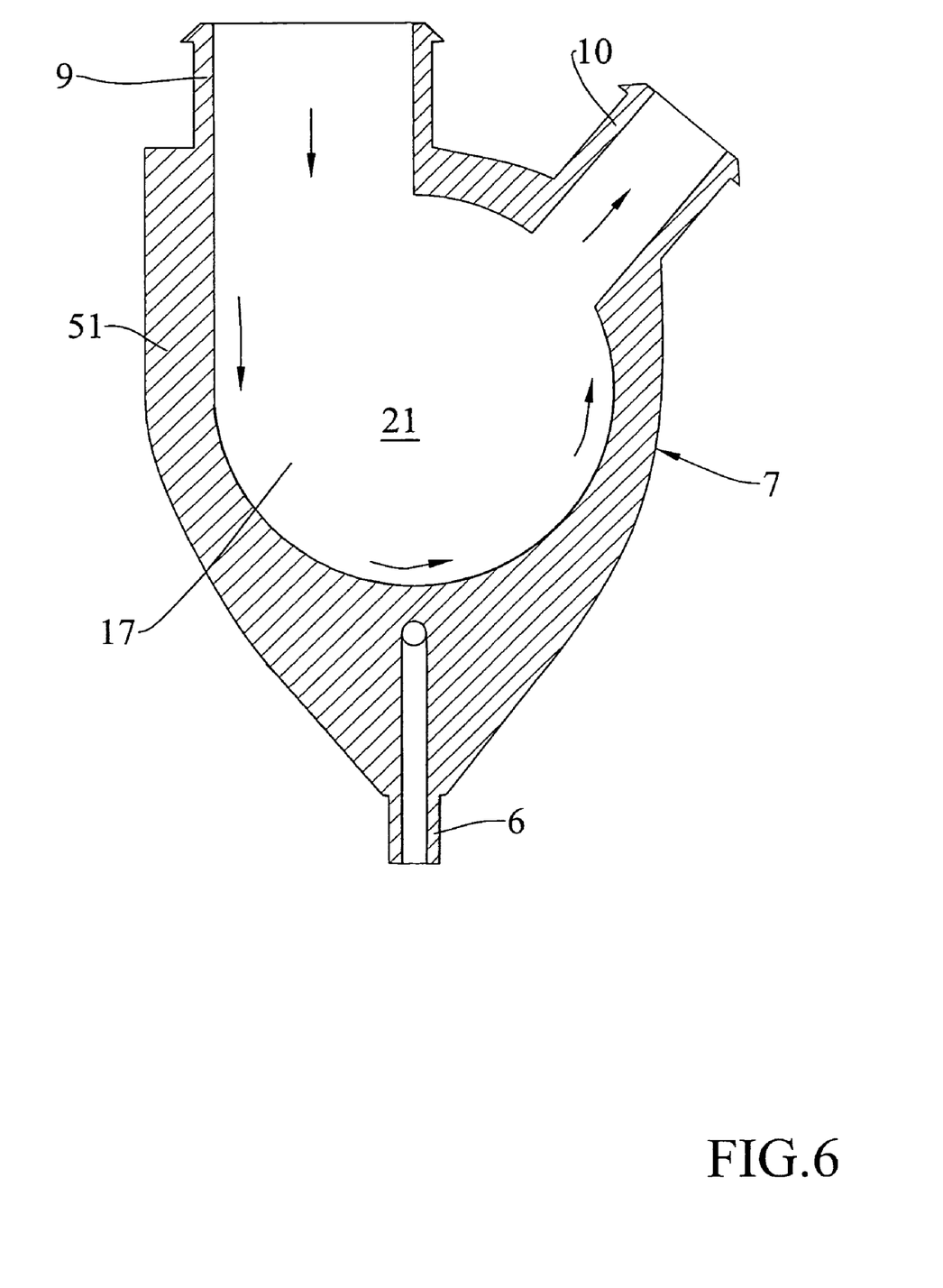
FIG. 6 shows the haematic pump in longitudinal section according to line VI-VI of FIG. 3.
Figure 7:
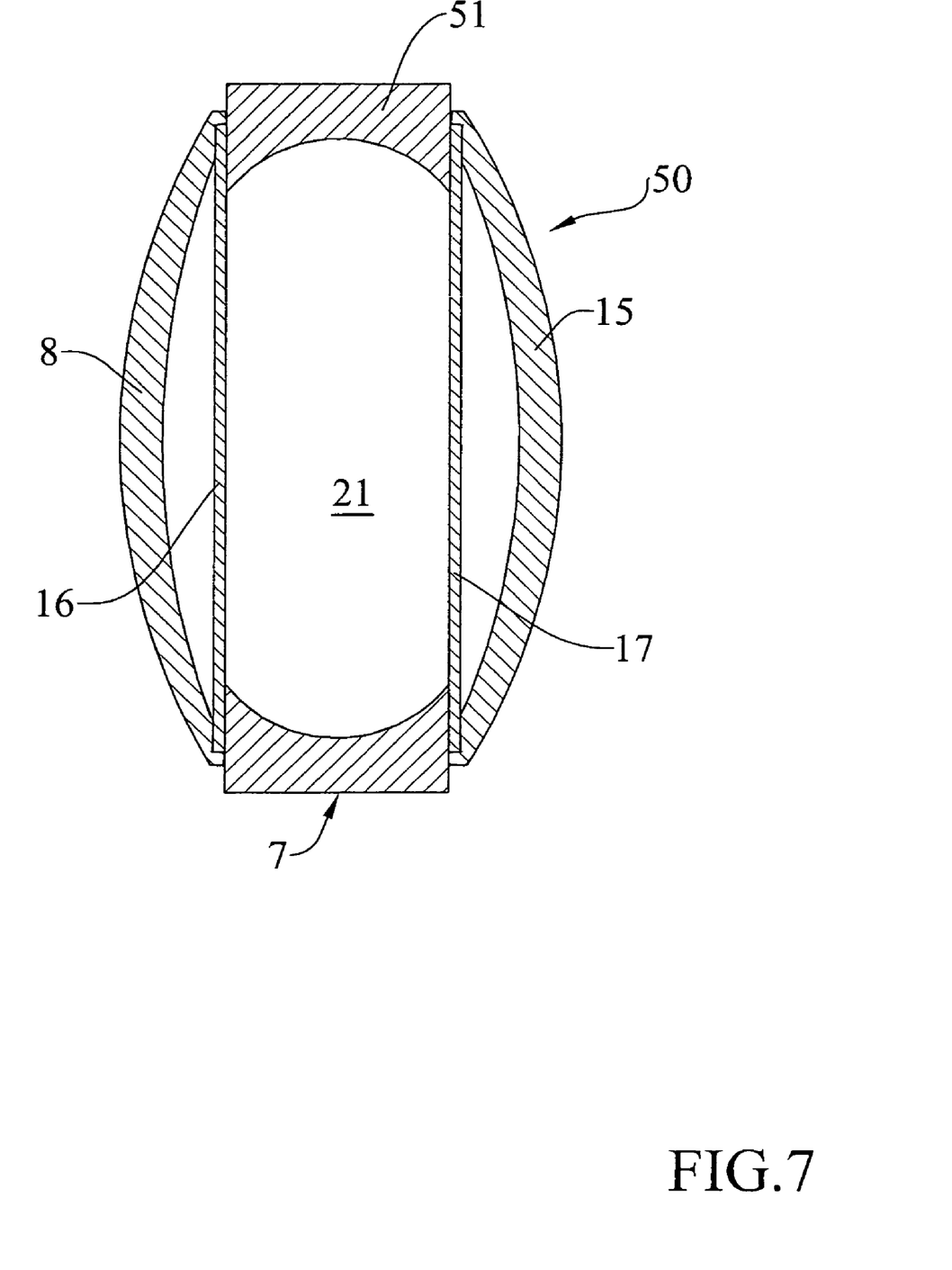
FIG. 7 shows the haematic pump sectioned along line VII-VII of FIG. 3.

Note that the substantially cylindrical inner conformation, with circular or elliptical bases, of space 21, clearly shown in FIG. 6, in combination with an appropriate processing of its inner surface, allows blood to move from the inlet 9 to the outlet 10 following a circular path skimming the inner wall of the space itself, exerting a continuous washing of the same and avoiding the formation of stasis and particular stresses for the molecules and substances residing in the blood, which may generate dangerous circumstances for the health of the patient.

Furthermore, the two mobile membranes 16 and 17 are designed so that the value of their inertial masses and accelerations is such that the inertial forces existing in the haematic pump cancel each other so as to generate a sum of forces equal to zero or very close to zero, thus avoiding sussultatory motions caused by inertial forces.

The function of the operating gas and the role carried out by external pneumatic energy generating unit 1 of FIG. 1 are now apparent. The operating gas used to compress inner membranes 16 and 17 of pump 50 is shifted by periodic alternate motion in alternate input/output direction to/from the haematic pump by means of a positive pressure/negative pressure generated by external unit 1.

This external unit is obtained with reduced weight and reduced size features so as to facilitate its transport by the patient easily without using special equipment such as trolleys or other voluminous equipments. It may be carried on the shoulder back or attached to the trouser belt of the patient by appropriate systems.

In brief, the device for cardiocirculatory assistance according to the present invention is a device which is capable of shifting sufficient blood amounts, producing a pulsing blood flow with variable flow rate depending on the number of pulses per minute generated by the external pneumatic energy unit by means of the operating gas.

The special inner configuration of the pump allows a particularly efficient and effective haematic flow also to be obtained as well as on the whole a device having no inertial sussultatory motions, where the periodic pulsing haematic flow provides pulses which may be synchronous or asynchronous with respect to the heart beat, the whole being driven by a small sized pneumatic energy generator.

The pulses generated may thus create the blood pumping state having pulsing motion synchronous to the heart beat, which is a specific feature of this invention.

It is known that the pumping of blood having a pulsing motion is much more physiological than the continuous motion obtained by currently existing centrifugal pumping systems.

Many minor modifications, not affecting the general principle at the basis of the present invention may of course be made to the above described device by way of example.

Specifically, valves 12 and 14 of FIG. 1 may be housed inside blood suction and delivery inlet 9 and outlet 10, instead of being inserted in tubings 11 and 13.

The inlet 9 and outlet 10 may in turn be reciprocally angled or parallel.

When the two membranes are in resting position, they may lie on reciprocally parallel planes, as shown in FIG. 3, or on reciprocally diverging planes in the direction of inlet 9 and outlet 10.

The invention claimed is:

1. A device for cardiocirculatory assistance comprising:
   a haematic pump with a pump body having an inner space defined by an external rigid structure and by a pair of internal flexible membranes arranged so as to oppose each other, each of said flexible membranes having a substantially circular shape;
   a pair of rigid lids arranged so as to define recesses between said rigid lids and said flexible membranes, respectively, wherein said recesses are to be alternately supplied with positive pressure and negative pressure gas so as to alternately draw said flexible membranes reciprocally together and apart in order to respectively decrease and increase a volume of said inner space of said pump body;
   a blood input tube connected to said pump body so as to be in fluid communication with said inner space of said pump body;
   a blood output tube connected to said pump body so as to be in fluid communication with said inner space; and
   a pair of spontaneously opening one-way valves for controlling a flow of blood through said blood input tube and said blood output tube, respectively, so as to allow, in combination with the increase and decrease of the volume of said inner space, a continuous filling and evacuating cycle of said inner space in which blood in said inner space flows along a substantially circular path defined by the substantially circular shape of said flexible membranes.

2. A device according to claim 1, wherein said inner space of said pump body has a blood input inlet and a blood output outlet connected to said blood input tube and said blood output tube, respectively.

3. A device according to claim 2, wherein said flexible membranes are arranged such that, when in a resting position, said flexible membranes lie on reciprocally divergent planes in a direction of said blood input inlet and said blood output outlet.

4. A device according to claim 1, wherein said flexible membranes are arranged such that, when in a resting position, said flexible membranes lie on reciprocally parallel planes.

5. A device according to claim 1, wherein said flexible membranes have substantially equal inertial masses.

6. A device according to claim 1, wherein said valves are arranged inside said blood input tube and said blood output tube, respectively.

7. A device according to claim 2, wherein said valves are arranged inside said blood input inlet and said blood output outlet, respectively.

8. A device according to claim 2, wherein said blood input inlet and said blood output outlet have reciprocally angled axes.

9. A device according to claim 2, wherein said blood input inlet and said blood output outlet have reciprocally parallel axes.

10. A device according to claim 1, wherein said pump body, said flexible membranes, said blood input inlet, said blood output outlet, said blood input tube, said blood output tube and said valves are all formed of haemocompatible material.

11. A device according to claim 1, further comprising:
    an external pneumatic energy generating unit for alternately supplying said recesses with positive pressure and negative pressure gas, wherein said recesses of said haematic pump are connected to the external pneumatic energy generating unit by a tube arranged within a body of a patient, a transcutaneous implant and a flexible external tube.

12. A device according to claim 1, further comprising:
    an external pneumatic energy generating unit for alternately supplying said recesses with positive pressure and negative pressure gas, wherein the external pneumatic energy generating unit is adapted to generate alternate positive pressures and negative pressures at a variable frequency so as to correspondingly vary the blood flow rate of the pump depending on needs of a patient.

13. A device according to claim 1, further comprising:
    an external pneumatic energy generating unit for alternately supplying said recesses with positive pressure and negative pressure gas, wherein the external pneumatic energy generating unit has a size such that it may be easily carried by a patient with the aid of a belt or a rucksack.

14. A device according to claim 2, wherein said flexible membranes are arranged such that, when in a resting position, said flexible membranes lie on reciprocally parallel planes.

15. A device according to claim 2, wherein said flexible membranes have substantially equal inertial masses.

16. A device according to claim 3, wherein said flexible membranes have substantially equal inertial masses.

17. A device according to claim 4, wherein said flexible membranes have substantially equal inertial masses.

18. A device according to claim 14, wherein said flexible membranes have substantially equal inertial masses.

19. A device according to claim 2, wherein said valves are arranged inside said blood input tube and said blood output tube, respectively.

20. A device according to claim 3, wherein said valves are arranged inside said blood input tube and said blood output tube, respectively.

* * * * *